(12) United States Patent
Dufresne et al.

(10) Patent No.: US 7,622,501 B2
(45) Date of Patent: Nov. 24, 2009

(54) NITRIC OXIDE RELEASING PRODRUGS OF DIARYL-2-(5H)-FURANONES AS CYCLOOXYGENASE-2 INHIBITORS

(75) Inventors: Claude Dufresne, Dollard-des-Ormeaux (CA); Carl Berthelette, Ste-Dorothee Laval (CA); Lianhai Li, Montreal (CA); Daniel Guay, Vaudreuil-Dorion (CA); Michel Gallant, Kirkland (CA); Patrick Lacombe, Montreal (CA); Renee Aspiotis, Kirkland (CA); Zhaoyin Wang, Kirkland (CA); Claudio F. Sturino, L'ile-Bizard (CA)

(73) Assignee: Merck Frosst Canada & Co., Kirkland, Province of Quebec (CA)

( * ) Notice: Subject to any disclaimer, the term of this patent is extended or adjusted under 35 U.S.C. 154(b) by 537 days.

(21) Appl. No.: 10/586,381

(22) PCT Filed: Jan. 25, 2005

(86) PCT No.: PCT/CA2005/000083

§ 371 (c)(1),
(2), (4) Date: Jul. 18, 2006

(87) PCT Pub. No.: WO2005/070883

PCT Pub. Date: Aug. 4, 2005

(65) Prior Publication Data

US 2008/0242643 A1     Oct. 2, 2008

Related U.S. Application Data

(60) Provisional application No. 60/539,666, filed on Jan. 27, 2004.

(51) Int. Cl.
*A61K 31/60* (2006.01)
(52) U.S. Cl. ........................ 514/509; 514/165; 514/533; 558/275; 560/11
(58) Field of Classification Search ................. 514/165, 514/533, 509; 560/11
See application file for complete search history.

(56) References Cited

U.S. PATENT DOCUMENTS 7,199,154 B2 *   4/2007   Berthelette et al. .......... 514/509

FOREIGN PATENT DOCUMENTS

| WO | WO 95/30641 | 11/1995 |
|---|---|---|
| WO | WO 97/28120 | 8/1997 |
| WO | WO 98/09948 | 3/1998 |
| WO | WO 01/45703 | 6/2001 |
| WO | WO 03/084550 | 10/2003 |
| WO | WO 03/103602 | 12/2003 |
| WO | WO 2004/002420 | 1/2004 |
| WO | WO 2004/011421 | 2/2004 |
| WO | WO 2004/103955 | 12/2004 |

* cited by examiner

*Primary Examiner*—Kamal A Saeed
*Assistant Examiner*—Valerie Rodriguez-Garcia
(74) *Attorney, Agent, or Firm*—Curtis C. Panzer; Valerie J. Camara

(57) ABSTRACT

The invention encompasses novel compounds of Formula I, which are nitric oxide-releasing prodrugs of diaryl-2-(5H)-furanones useful in the treatment of cyclooxygenase-2 mediated diseases, Formula (I). The invention also encompasses certain pharmaceutical compositions and methods for treating cyclooxygenase-2 mediated diseases comprising the use of compounds of Formula 1. The above compounds may be used as a combination therapy with low-dose aspirin to treat chronic cyclooxygenase-2 mediated diseases or conditions while also reducing the risk of thrombotic cardiovascular events.

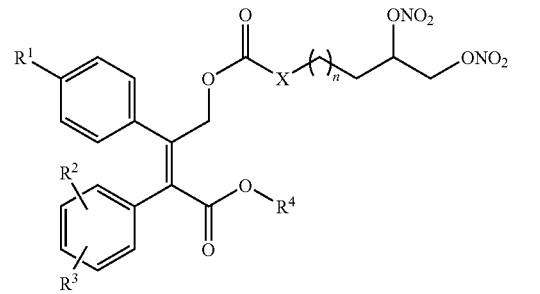

15 Claims, No Drawings

NITRIC OXIDE RELEASING PRODRUGS OF DIARYL-2-(5H)-FURANONES AS CYCLOOXYGENASE-2 INHIBITORS

CROSS REFERENCE TO RELATED APPLICATIONS

This application is a U.S. national phase application under 35 U.S.C. § 371 of PCT Application No. PCT/CA2005/000083, Jan. 25, 2005, which claims priority under 35 U.S.C. 119 to U.S. No. 60/539,666, filed Jan. 27, 2004.

BACKGROUND OF THE INVENTION

Selective inhibitors of cyclooxygenase-2 are a sub-class of the class of drugs known as non-steroidal antiinflammatory drugs (NSAIDs). The NSAIDs are active in reducing the prostaglandin-induced pain and swelling associated with the inflammation process but are also active in affecting other prostaglandin-regulated processes not associated with the inflammation process. Thus, use of high doses of most common NSAIDs can produce severe side effects, including life threatening ulcers, that limit their therapeutic potential. An alternative to NSAIDs is the use of corticosteroids, which have even more drastic side effects, especially when long term therapy is involved.

Previous NSAIDs have been found to prevent the production of prostaglandin by inhibiting enzymes in the human arachidonic acid/prostaglandin pathway including the enzyme cyclooxygenase (COX). The discovery that there are two isoforms of the COX enzyme, the first, COX-1, being involved with physiological functions and the second, COX-2, being induced in inflamed tissue, has given rise to a new approach. While conventional NSAIDs block both forms of the enzyme, the identification of the inducible COX-2 enzyme associated with inflammation has provided a viable target of inhibition which more effectively reduces inflammation and produces fewer and less drastic side effects. Many compounds which have activity as COX-2 inhibitors have been identified, including rofecoxib (VIOXX®), etoricoxib (ARCOXIA™), celecoxib (CELEBREX®) and valdecoxib (BEXTRA™), and much research continues in this area.

Many patients suffering from a chronic cyclooxygenase-2 mediated disease or condition are elderly and thus are at increased risk for thrombotic cardiovascular events, such as stroke, myocardial ischemia, myocardial infarction, angina pectoris, transient ischemic attack (TIA; amaurosis fugax), reversible ischemic neurologic deficits, and any similar thrombotic event in any vascular bed (splanchnic, renal, aortic, peripheral, etc.). Moreover, there is evidence that patients with chronic inflammatory conditions, such as rheumatoid arthritis and systemic lupus erythematosis are at increased risk for thrombotic cardiovascular events. It is desirable that such patients receive appropriate therapy to reduce their risk of such events, such as low-dose aspirin therapy. However, it has been reported that the co-administration of aspirin and a selective COX-2 inhibitor in a rat model resulted in substantially more severe gastric injury than is produced with either agent alone. See Fiorucci et al., *Gastroenterology*, vol. 123, pp. 1598-1606, 2002. Thus, the major advantage that COX-2 selective inhibitors have over NSAIDS may be offset by the concomitant use of aspirin.

NO-releasing forms of non-steroidal anti-inflammatory drugs are known in the art and are reported to have improved gastrointestinal and cardiovascular safety profiles over their conventional NSAID counterparts. Furthermore, NO-releasing forms of selective cyclooxygenase-2 selective inhibitors are disclosed in WO 01/45703, published on Jun. 28, 2001.

The present invention provides for novel nitrosated prodrugs for cyclooxygenase-2 selective inhibitors that are useful for treating cyclooxygenase-2 mediated diseases or conditions and can be administered alone or in combination with low-dose aspirin. The invention provides efficacy in treating chronic cyclooxygenase-2 mediated diseases or conditions, effectively reduces the risk of thrombotic cardiovascular events and potentially renal side effects and at the same time reduces the risk of GI ulceration or bleeding.

SUMMARY OF THE INVENTION

The invention encompasses novel compounds of Formula I, which are nitric oxide-releasing prodrugs of diaryl-2-(5H) furanones useful in the treatment of cyclooxygenase-2 mediated diseases:

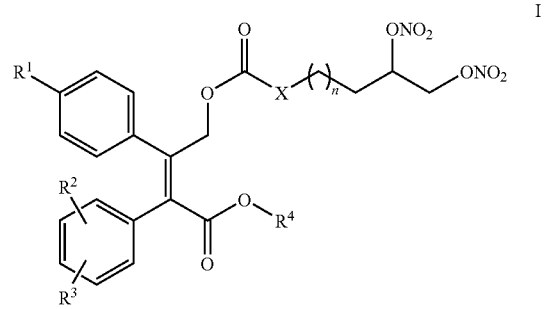

The invention also encompasses certain pharmaceutical compositions and methods for treating cyclooxygenase-2 mediated diseases comprising the use of compounds of Formula I. The above compounds may be used as a combination therapy with low-dose aspirin to treat chronic cyclooxygenase-2 mediated diseases or conditions while also reducing the risk of thrombotic cardiovascular events.

DETAILED DESCRIPTION OF THE INVENTION

The invention encompasses novel compounds of Formula I as prodrugs that convert in vivo to diaryl-2-(5H)-furanones and useful in the treatment of cyclooxygenase-2 mediated diseases:

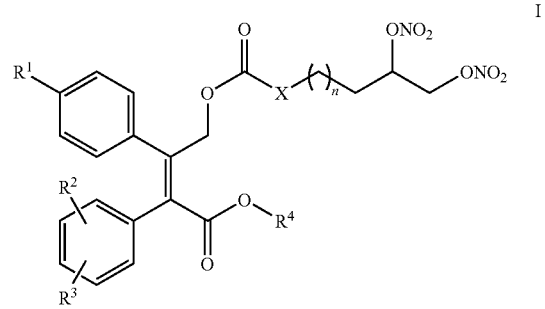

or a pharmaceutically acceptable salt thereof, wherein:
n is an integer from 1 to 6;
X is —O— or —$CH_2$—;
$R^1$ is selected from the group consisting of:

(a) S(O)$_2$CH$_3$ and
(b) S(O)$_2$NH$_2$;

R$^2$ and R$^3$ each are independently selected from the group consisting of:
(a) hydrogen,
(b) halo,
(c) C$_{1-6}$alkoxy,
(d) C$_{1-6}$alkylthio,
(e) CN,
(f) CF$_3$,
(g) C$_{1-6}$alkyl, and
(h) N$_3$;

R$^4$ is selected from the group consisting of
(a) hydrogen,
(b) —C$_{1-4}$alkyl, optionally substituted with 1 to 3 substituents independently selected from halo and R$^5$, and
(c) R$^5$;

each R$^5$ is independently selected from the group consisting of: phenyl, naphthyl or a 5- or 6-membered aromatic heterocycle, each optionally substituted with 1 to 3 halo groups.

An embodiment of the invention encompasses a compound of Formula I wherein R$^1$ is S(O)$_2$CH$_3$, and R$^2$ and R$^3$ are both hydrogen.

Another embodiment of the invention encompasses a compound of Formula I wherein n is 1; 2 or 3.

Another embodiment of the invention encompasses a compound of Formula I wherein R$^4$ is selected from the group consisting of: hydrogen, methyl, ethyl and benzyl.

Another embodiment of the invention encompasses a compound of Formula I wherein X is —O—.

The invention also encompasses a pharmaceutical composition comprising a compound of Formula I and a pharmaceutically acceptable carrier.

The invention also encompasses a method of treating an inflammatory disease susceptible to treatment with a non-steroidal anti-inflammatory agent comprising administering to a patient in need of such treatment of a non-toxic therapeutically effective amount of a compound of Formula I. Within this embodiment is encompassed the above method wherein the patient is also at risk of a thrombotic cardiovascular event and the patient is on aspirin therapy to reduce the risk of the cardiovascular event.

Another embodiment of the invention encompasses a method of treating cyclooxygenase mediated diseases advantageously treated by an active agent that selectively inhibits COX-2 in preference to COX-1 comprising administering to a patient in need of such treatment of a non-toxic therapeutically effective amount of a compound of Formula I. Within this embodiment is encompassed the above method wherein the patient is also at risk of a thrombotic cardiovascular event and the patient is on aspirin therapy to reduce the risk of the cardiovascular event.

Another embodiment of the invention encompasses a method for treating a chronic cyclooxygenase-2 mediated disease or condition and reducing the risk of a thrombotic cardiovascular event in a human patient in need of such treatment and at risk of a thrombotic cardiovascular event comprising orally concomitantly or sequentially administering to said patient a compound of Formula I in an amount effective to treat the cyclooxygenase-2 mediated disease or condition and aspirin in an amount effective to reduce the risk of the thrombotic cardiovascular event. Within this embodiment is encompassed the above method wherein the compound of Formula I is administered orally on a once daily basis. Within this embodiment is encompassed the above method wherein the compound of Formula I is administered orally on a twice daily basis. Within this embodiment is encompassed the above method wherein the cyclooxygenase-2 selective mediated disease or condition is selected from the group consisting of: osteoarthritis, rheumatoid arthritis and chronic pain. Within this embodiment is encompassed the above method wherein aspirin is administered at a dose of about 30 mg to about 1 g. Within this embodiment is encompassed the above method wherein aspirin is administered at a dose of about 80 to about 650 mg. Within this embodiment is encompassed the above method wherein aspirin is administered at a dose of about 81 mg or about 325 mg. Within this embodiment is encompassed the above method wherein aspirin is orally administered once daily.

The invention also encompasses a pharmaceutical composition comprising a compound of Formula I and aspirin in combination with a pharmaceutically acceptable carrier.

The term "halogen" or "halo" includes F, Cl, Br, and I.

The term "alkyl" means linear or branched structures and combinations thereof, having the indicated number of carbon atoms. Thus, for example, C$_{1-6}$alkyl includes methyl, ethyl, propyl, 2-propyl, s- and t-butyl, butyl, pentyl, hexyl, 1,1-dimethylethyl, cyclopropyl, cyclobutyl, cyclopentyl and cyclohexyl.

The term "alkoxy" means alkoxy groups of a straight or branched configuration having the indicated number of carbon atoms. C$_{1-6}$alkoxy, for example, includes methoxy, ethoxy, propoxy, isopropoxy, and the like.

The term "alkylthio" means alkylthio groups having the indicated number of carbon atoms of a straight or branched configuration. C$_{1-6}$alkylthio, for example, includes methylthio, propylthio, isopropylthio, and the like.

The term "5- or 6-membered aromatic heterocycle" means for example, pyrrole, furan, thiophene, imidazole, pyrazole, oxazole, isoxazole, thiazole, isothiazole, triazole, oxadiazole, thiadiazole, tetrazole, pyridine, pyrimidine, pyrazine, pyridazine and triazine.

Some of the compounds described herein contain olefinic double bonds, and unless specified otherwise, are meant to include both E and Z geometric isomers. Compounds of Formula I may contain one or more asymmetric centers and can thus occur as racemates and racemic mixtures, single enantiomers, diastereomeric mixtures and individual diastereomers. The present invention is meant to comprehend all such isomeric forms of the compounds of Formula I.

The term "treating a chronic cylcooxygenase-2 mediated disease or condition" means treating or preventing any chronic disease or condition that is advantageously treated or prevented by inhibiting the cyclooxygenase-2 enzyme. The term includes the relief of pain, fever and inflammation of a variety of conditions including rheumatic fever, symptoms associated with influenza or other viral infections, common cold, low back and neck pain, dysmenorrhea, headache, migraine (acute and prophylactics treatment), toothache, sprains and strains, myositis, neuralgia, synovitis, arthritis, including rheumatoid arthritis, degenerative joint diseases (osteoarthritis), gout and ankylosing spondylitis, acute, subacute and chronic musculoskeletal pain syndromes such as bursitis, burns, injuries, and pain following surgical and dental procedures as well as the preemptive treatment of surgical pain. In addition, the term includes the inhibition cellular neoplastic transformations and metastic tumor growth and hence the treatment of cancer. The term also includes the treatment of endometriosis and Parkinson's disease as well as the treatment of cyclooxygenase-mediated proliferative disorders such as may occur in diabetic retinopathy and tumor angiogenesis. The term "treating" encompasses not only treating a patient to relieve the patient of the signs and symptoms of the disease or condition but also prophylactically treating an asymptomatic patient to prevent the onset or progression of the disease or condition.

A "thrombotic cardiovascular event" is defined as any sudden event of a type known to be caused by platelet aggregation, thrombosis, and subsequent ischemic clinical events, including thrombotic or thromboembolic stroke, myocardial ischemia, myocardial infarction, angina pectoris, transient ischemic attack (TIA; amaurosis fugax), reversible ischemic neurologic deficits, and any similar thrombotic event in any vascular bed (splanchnic, renal, aortic, peripheral, etc.).

The term "patient in need of such treatment and at risk of a thrombotic cardiovascular event" means a patient in need of both treatment for a cyclooxygenase-2 mediated disease and also at risk of a thrombotic cardiovascular event. One skilled in the art can diagnose a patient that is in need of treatment for a cyclooxygenase-2 mediated disease or condition and also at risk of suffering a thrombotic cardiovascular event. For example, such a patient may be over the age of 50 with osteoarthritis and with a previous myocardial infarction. Other risk factors for a thrombotic cardiovascular event include hypertension, hypercholesterolemia, diabetes mellitus, chronic renal impairment, smoking, and any prior personal or family history of such an event. Administration of the drug combination to the patient includes both self-administration and administration to the patient by another person.

The term "amounts that are effective to treat" is intended to mean that amount of a drug or pharmaceutical agent that will elicit the biological or medical response of a tissue, a system, animal or human that is being sought by a researcher, veterinarian, medical doctor or other clinician. The term also encompasses the amount of a pharmaceutical drug that will prevent or reduce the risk of occurrence of the biological or medical event that is sought to be prevented in a tissue, a system, animal or human by a researcher, veterinarian, medical doctor or other clinician. The inhibitor of cyclooxygenase-2 may be administered at a dosage level up to conventional dosage levels for NSAIDs. Suitable dosage levels of the compound of Formula I used in the present invention are described below. The compound may be administered on a regimen of once or twice per day.

The term "amount effective to reduce the risk of" means the amount of a pharmaceutical drug that will prevent or reduce the risk of occurrence of the biological or medical event that is sought to be prevented in a tissue, a system, animal or human by a researcher, veterinarian, medical doctor or other clinician. Aspirin is administered at a dose of about 30 mg to about 1 g once daily, preferably at a dose of about 80 mg to about 650 mg.

The term "concomitantly administering" means administering the agents substantially concurrently. The term "concomitantly administering" encompasses not only administering the two agents in a single pharmaceutical dosage form but also the administration of each active agent in its own separate pharmaceutical dosage formulation. Where separate dosage formulations are used, the agents can be administered at essentially the same time, i.e., concurrently.

The term "sequentially administering" means administering the agents at separately staggered times. Thus, agents can be sequentially administered such that the beneficial pharmaceutical effect of aspirin and a compound of the present invention are realized by the patient at substantially the same time. Thus, for example, if a compound of the present invention and aspirin are both administered on a once a day basis, the interval of separation between sequential administration of the two agents can be up to twelve hours apart.

The pharmaceutical compositions of the present invention comprise a compound of Formula I as an active ingredient or a pharmaceutically acceptable salt, thereof, and may also contain a pharmaceutically acceptable carrier and optionally other therapeutic ingredients. The term "pharmaceutically acceptable salts" includes salts prepared from bases that result in non-toxic pharmaceutically acceptable salts, including inorganic bases and organic bases. Salts derived from inorganic bases include aluminum, ammonium, calcium, copper, ferric, ferrous, lithium, magnesium, manganic salts, manganous, potassium, sodium, zinc, and the like. Particularly preferred are the ammonium, calcium, magnesium, potassium, and sodium salts. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like.

When the compound of the present invention is basic, salts may be prepared from acids that result in pharmaceutically acceptable salts, including inorganic and organic acids. Such acids include acetic, adipic, aspartic, 1,5-naphthalenedisulfonic, benzenesulfonic, benzoic, camphorsulfonic, citric, 1,2-ethanedisulfonic, ethanesulfonic, ethylenediaminetetraacetic, fumaric, glucoheptonic, gluconic, glutamic, hydriodic, hydrobromic, hydrochloric, isethionic, lactic, maleic, malic, mandelic, methanesulfonic, mucic, 2-naphthalenesulfonic, nitric, oxalic, pamoic, pantothenic, phosphoric, pivalic, propionic, salicylic, stearic, succinic, sulfuric, tartaric, p-toluenesulfonic acid, undecanoic, 10-undecenoic, and the like.

The compounds of Formula I are prodrugs of cyclooxygenase-2 selective inhibitors which covert in vivo to diaryl-2-(5H)-furanones. The compounds also liberate nitric oxide in vivo, which is believed to contribute to an improved gastrointestinal and potentially renal safety profile. As such, the compounds of the present invention may be co-dosed with low-dose aspirin to treat chronic cyclooxygenase-2 mediated diseases or conditions, effectively reduce the risk of thrombotic cardiovascular events and potentially renal side effects and at the same time reduce the risk of GI ulceration or bleeding. Thus, patients with hypertension and cardiovascular disease, as well as potentially patients with renal insufficiency, would actively benefit from being administered compounds of the present invention over NSAIDs and cyclooxygenase-2 selective inhibitors currently available.

By virtue of the cyclooxygenase-2 activity of the active moiety of the prodrugs of the present invention, the compounds of Formula I are therefore useful for the relief of pain, fever and inflammation of a variety of conditions including rheumatic fever, symptoms associated with influenza or other viral infections, common cold, low back and neck pain, dysmenorrhea, headache, migraine (acute and prophylactice treatment), toothache, sprains and strains, myositis, neuralgia, synovitis, arthritis, including rheumatoid arthritis, degenerative joint diseases (osteoarthritis), gout and ankylosing spondylitis, acute, subacute and chronic musculoskeletal pain syndromes such as bursitis, burns, injuries, and pain following surgical and dental procedures as well as the preemptive treatment of surgical pain. In addition, such a compound may inhibit cellular neoplastic transformations and metastic tumor growth and hence can be used in the treatment of cancer. Compounds of Formula I may also be useful for the treatment or prevention of endometriosis and Parkinson's disease.

Compounds of Formula I will also inhibit prostanoid-induced smooth muscle contraction by preventing the synthesis of contractile prostanoids and hence may be of use in the treatment of dysmenorrhea, premature labor and asthma.

By virtue of the high cyclooxygenase-2 (COX-2) activity and/or the selectivity for cyclooxygenase-2 over cyclooxygenase-1 (COX-1) of the active moiety of the prodrugs of the invention as defined above, compounds of Formula I will prove useful as an alternative to conventional non-steroidal antiinflammatory drugs (NSAID'S) particularly where such non-steroidal antiinflammatory drugs may be contra-indicated such as in patients with peptic ulcers, gastritis, regional enteritis, ulcerative colitis, diverticulitis or with a recurrent history of gastrointestinal lesions; GI bleeding, coagulation disorders including anemia such as hypoprothrombinemia, haemophilia or other bleeding problems (including those relating to reduced or impaired platelet function); kidney disease (e.g. impaired renal function); those prior to surgery or taking anticoagulants; and those susceptible to NSAID induced asthma.

Similarly, compounds of Formula I will be useful as a partial or complete substitute for conventional NSAIDs in preparations wherein they are presently co-administered with other agents or ingredients. Thus in further aspects, the invention encompasses pharmaceutical compositions for treating cyclooxygenase-2 mediated diseases as defined above comprising a non-toxic therapeutically effective amount of the compound of Formula I as defined above and one or more ingredients such as another pain reliever including acetominophen or phenacetin; opioid analgesics, such as codeine, fentanyl, hydromorphone, levorphanol, meperidine, methadone, morphine, oxycodone, oxymorphine, propoxyphene, buprenorphine, butorphanol, dezocine, nalbuphine and pentazocine; a potentiator including caffeine; an H2-antagonist; aluminum or magnesium hydroxide; simethicone; a decongestant including phenylephrine, phenylpropanolamine, pseudophedrine, oxymetazoline, ephinephrine, naphazoline, xylometazoline, propylhexedrine, or levo-desoxyephedrine; an antitussive including codeine, hydrocodone, caramiphen, carbetapentane, or dextramethorphan; a diuretic; a sedating or non-sedating antihistamine; and a proton pump inhibitor, such as omeprazole. For the treatment or prevention of migraine, the invention also encompasses co-administration with a 5-HT agonist such as rizatriptan, sumatriptan, zolmitriptan and naratriptan. In addition the invention encompasses a method of treating cyclooxygenase mediated diseases comprising: administration to a patient in need of such treatment a non-toxic therapeutically effect amount of the compound of Formula I, optionally co-administered with one or more of such ingredients as listed immediately above.

Compounds of the present invention are prodrugs of inhibitors of cyclooxygenase-2 and are thereby useful in the treatment of cyclooxygenase-2 mediated diseases as enumerated above. This activity is illustrated by their ability to selectively inhibit cyclooxygenase-2 over cyclooxygenase-1. Accordingly, the ability of the compounds of this invention to convert to the active compound and thus treat cyclooxygenase mediated diseases can be demonstrated by measuring the amount of prostaglandin $E_2$ ($PGE_2$) synthesized in the presence of arachidonic acid, cyclooxygenase-1 or cyclooxygenase-2 and a compound of Formula I as illustrated in the assays that follow. The $IC_{50}$ values represent the concentration of inhibitor required to return $PGE_2$ synthesis to 50% of that obtained as compared to the uninhibited control. For the treatment of any of these cyclooxygenase mediated diseases, compounds of Formula I may be administered orally, topically, parenterally, by inhalation spray or rectally in dosage unit formulations containing conventional non-toxic pharmaceutically acceptable carriers, adjuvants and vehicles. Compounds of the invention may be administered via the buccal or sublingual mucosa in the oral cavity. The term parenteral as used herein includes subcutaneous injections, intravenous, intramuscular, intrasternal injection or infusion techniques. Compounds of the invention may also be administered through the nasal, pulmonary (inhalation aerosol) or ocular route. In addition to the treatment of warm-blooded animals such as mice, rats, horses, cattle, sheep, dogs, cats, etc., the compound of the invention is effective in the treatment of humans.

As indicated above, pharmaceutical compositions for treating cyclooxygenase-2 mediated diseases as defined may optionally include one or more ingredients as listed above.

The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example, magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the technique described in the U.S. Pat. Nos. 4,256, 108; 4,166,452; and 4,265,874 to form osmotic therapeutic tablets for control release.

Formulations for oral use may also be presented as hard gelatin capsules wherein the active ingredient is mixed with an inert solid diluent, for example, calcium carbonate, Calcium phosphate or kaolin, or as soft gelatin capsules wherein the active ingredients is mixed with water or an oil medium, for example peanut oil, liquid paraffin, or olive oil.

Aqueous suspensions contain the active material in admixture with excipients suitable for the manufacture of aqueous suspensions. Such excipients are suspending agents, for example sodium carboxymethyl-cellulose, methylcellulose, hydroxypropylmethyl-cellulose, sodium alginate, polyvinylpyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more coloring agents, one or more flavoring agents, and one or more sweetening agents, such as sucrose, saccharin or aspartame.

Liquid formulations include the use of self-emulsifying drug delivery systems and NanoCrystal® technology. Cyclodextrin inclusion complexes can also be utilized.

Oily suspensions may be formulated by suspending the active ingredient in a vegetable oil, for example arachis oil, olive oil, sesame oil or coconut oil, or in mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

The pharmaceutical compositions of the invention may also be in the form of an oil-in-water emulsions. The oily phase may be a vegetable oil, for example olive oil or arachis oil, or a mineral oil, for example liquid paraffin or mixtures of these. Suitable emulsifying agents may be naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavouring agents.

Syrups and elixirs may be formulated with sweetening agents, for example glycerol, propylene glycol, sorbitol or sucrose. Such formulations may also contain a demulcent, a preservative and flavoring and coloring agents. The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

Compounds of Formula I may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

For topical use, creams, ointments, jellies, solutions or suspensions, etc., containing the compound of Formula I are employed. (For purposes of this application, topical application shall include mouth washes and gargles.)

Pharmaceutical compositions of the invention may also utilize absorption enhancers such as tween 80, tween 20, Vitamin E TPGS (d-alpha-tocopheryl polyethylene glycol 1000 succinate) and Gelucire®.

Dosage levels of the order of from about 0.01 mg to about 140 mg/kg of body weight per day are useful in the treatment of the above-indicated conditions, or alternatively about 0.5 mg to about 7 g per patient per day. For example, inflammation may be effectively treated by the administration of from about 0.01 to 50 mg of the compound per kilogram of body weight per day, or alternatively about 0.5 mg to about 3.5 g per patient per day, preferably 2.5 mg to 1 g per patient per day.

The amount of active ingredient that may be combined with the carrier materials to produce a single dosage form will vary depending upon the host treated and the particular mode of administration. For example, a formulation intended for the oral administration of humans may contain from 0.5 mg to 5 g of active agent compounded with an appropriate and convenient amount of carrier material which may vary from about 5 to about 95 percent of the total composition. Dosage unit forms will generally contain between from about 1 mg to about 500 mg of an active ingredient, typically 25 mg, 50 mg, 100 mg, 200 mg, 300 mg, 400 mg, 500 mg, 600 mg, 800 mg, or 1000 mg.

It will be understood, however, that the specific dose level for any particular patient will depend upon a variety of factors including the age, body weight, general health, sex, diet, time of administration, route of administration, rate of excretion, drug combination and the severity of the particular disease undergoing therapy.

Methods of Synthesis

Stilbene derivatives useful as cyclooxygenase-2 selective inhibitors are disclosed in U.S. Pat. No. 5,849,943, which is hereby incorporate by reference in its entirety.

Diaryl-2-(5H)-furanones useful as COX-2 inhibitors are known in the art and disclosed in U.S. Pat. No. 5,474,995, which is hereby incorporated by reference in its entirety. Methods for making diaryl-2-(5H)-furanones useful as COX-2 inhibitors are disclosed in U.S. Pat. No. 5,840,924, which is hereby incorporated by reference in its entirety. Rofecoxib, sold under the tradename VIOXX, is known in the art and commercially available.

Compounds of the invention can be synthesized according to the following synthetic scheme:

Scheme 1

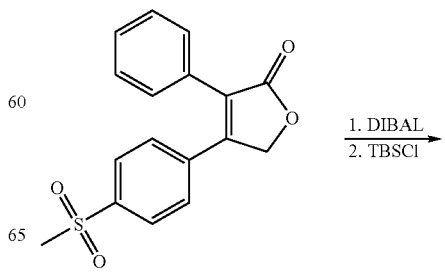

-continued

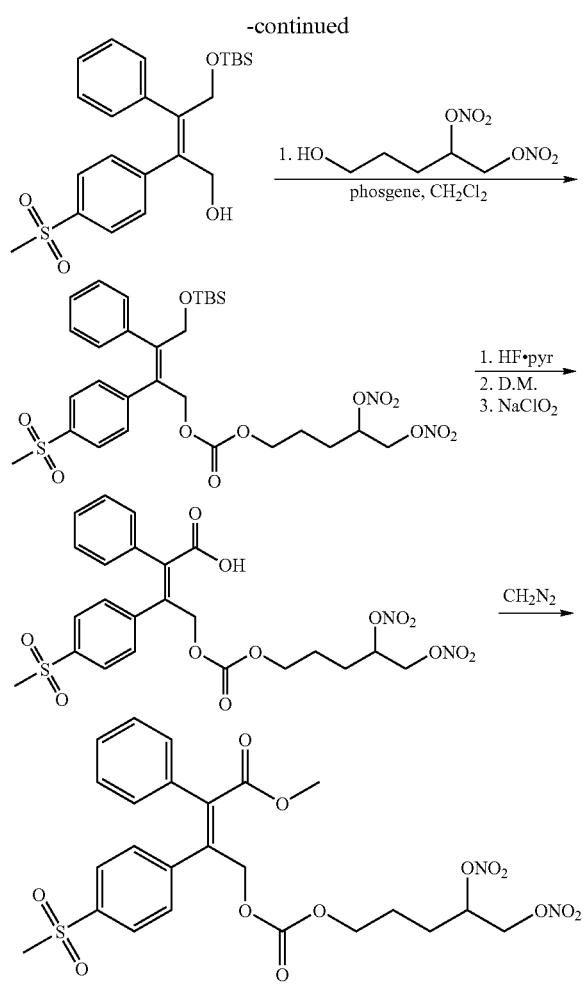

Abbreviations used in Scheme 1
D.M.=Dess-Martin reagent
HF.pyr=hydrogen fluoride pyridine (70/30)

Assays for Determining Biological Activity

The compound of Formula I can be tested using the following assays to determine their biological activity.

Inhibition of Cyclooxygenase Activity

Compounds are tested as inhibitors of cyclooxygenase activity in whole cell and microsomal cyclooxygenase assays. Both of these assays measure prostaglandin $E_2$ (PGE$_2$) synthesis in response to arachidonic acid, using a radioimmunoassay. Cells used for whole cell assays, and from which microsomes are prepared for microsomal assays, are human osteosarcoma 143 cells (which specifically express cyclooxygenase-2) and human U-937 cells (which specifically express cyclooxygenase-1). In these assays, 100% activity is defined as the difference between prostaglandin $E_2$ synthesis in the absence and presence of arachidonate addition. IC$_{50}$ values represent the concentration of putative inhibitor required to return PGE$_2$ synthesis to 50% of that obtained as compared to the uninhibited control.

A. Microsomal Cyclooxygenase Assay

Cox microsomal fractions are prepared as previously described (Percival et al., Arch. Biochem. Biophys. (1994) 315:111-118). The enzyme reactions are performed in 50 mM KPi pH 8.0, 1 µM heme, 1 mM phenol supplemented with 10 µg/ml of each Cox-1 or Cox-2 microsomal fractions. 1 µl DMSO or test compound (100 fold stock concentrated in DMSO) are added to 100 µl buffer. The enzyme reaction is initiated 15 minutes later by the addition of 10 µl of 100 µM arachidonic acid. The enzyme reaction is allowed to proceed for 5 minutes at room temperature before being stopped by the addition of 10 µl 1 N HCl. PGE$_2$ levels are then determined by EIA (Assay Designs) using the manufacturer's instruction.

This assay may be used to demonstrate that the unconverted prodrugs of the instant invention are inactive against both COX-1 and COX-2.

B. Human Whole Blood Cyclooxygenase Assay

Rationale

Whole blood provides a protein and cell-rich milieu for the study of biochemical efficacy of anti-inflammatory compounds such as COX-2 inhibitors and NSAIDs. To study the inhibitory activities of these compounds on the two isoforms of cyclooxygenase (COX-1 and COX-2), human blood is either stimulated with lipopolysaccharide (LPS) for 24 hours to induce COX-2 or the blood is allowed to clot spontaneously to activate COX-1. The production of prostaglandin $E_2$ (PGE$_2$) and thromboxane $B_2$ (TXB$_2$) are measured by immunoassay at the end of the incubation as readouts of COX-2 and COX-1 activity, respectively.

Methods

Human whole blood assays for COX-1 and COX-2 activity, previously reported (Brideau et al, 1996) are performed as described below.

1. COX-2 (LPS-induced PGE$_2$ Production):

Fresh blood is collected in heparinized tubes by venipuncture from healthy male volunteers. These subjects have no apparent inflammatory conditions and have not taken any NSAIDs for at least 7 days prior to blood collection. The blood is initially pre-incubated with bacterial lipopolysaccharide (LPS) at 100 µg/ml (Sigma Chem, #L-2630 from E. coli, serotype 0111:B4; diluted in 0.1% w/v bovine serine albumin in phosphate buffered saline). Five minutes later, 500 µL aliquots of the LPS-treated blood are incubated with 2 µL vehicle (DMSO) or 2 µL of test compounds in DMSO for 24 hr at 37° C. (for induction of COX-2). Unstimulated control blood at time zero (no LPS) is used as blank. At the end of the 24 hr incubation, the blood is centrifuged at 3,000 rpms for 10 min at 40° C. to obtain plasma. The plasma is assayed for PGE$_2$ using an enzyme immunoassay kit (Assay Designs, 901-001) according to the manufacturer's instructions.

2. COX-1 (Clotting-Induced TXB2 Production):

Fresh blood from male or female volunteers is collected into vacutainers containing no anticoagulants. These subjects have no apparent inflammatory conditions and have not taken any NSAIDs for at least 7 days prior to blood collection. Aliquots of 500 µL are immediately transferred to polypropylene tubes preloaded with 2 µL of DMSO or 2 µL of test compounds. The tubes are vortexed and incubated at 37° C. for 1 h to allow the blood to clot. At the end of the incubation, serum is obtained by centrifugation (3,000 rpm for 10 min at 40° C.). The serum is obtained and is assayed for TXB$_2$ using an enzyme immunoassay kit (Assay Designs, 901-002) according to the manufacturer's instructions.

Representative Rat Paw Edema Assay—Protocol

Rationale

The carrageenan-induced rat paw edema assay is an established assay for evaluating the efficacy of conventional, nonselective NSAIDs in acute inflammation (Winter and Flataker, 1965; Mukherjee et al., 1996; Vinegar et al., 1987).

Methods

Male Sprague-Dawley rats (200-250 g) are fasted for 16-18 h prior to oral administration of either the vehicle (0.5% methocel) or test compound. One hour later, a line was drawn using a permanent marker at a level above the ankle in one hind paw to define the area of the paw to be monitored. The paw volume ($V_0$) is measured using a plethysmometer (Ugo-Basile, Italy) based on the Archimedes principle of water displacement. The rats are then injected subplantarly with 0.05 mL of a 1% carrageenan (Sigma Chem.) solution in saline using a syringe with a 27-gauge needle (i.e. 500 μg carrageenan per paw). Three hours later, the paw volume ($V_3$) is measured again and the increases in paw volume ($V_3-V_0$) is calculated. Paw edema is compared with the vehicle-control group and the percent inhibition calculated taking the values in the control group as 0%.

NSAID-Induced Gastropathy in Rats

Rationale

The major side effect of conventional NSAIDs is their ability to produce gastric lesions in man. Rats are sensitive to the actions of NSAIDs and have been used commonly in the past to evaluate the gastrointestinal side effects of current conventional NSAIDs. In the present assay, NSAID-induced gastrointestinal damage is observed by measuring urinary $^{51}Cr$ excretion after oral dosing of $^{51}Cr$-EDTA. Urinary $^{51}Cr$ excretion is a well-established and sensitive technique to detect gastrointestinal integrity in animals and man.

Methods

Male Sprague-Dawley rats (150-200 g) are administered orally a test compound either once (acute dosing) or in multiple doses for a few days (chronic dosing). Immediately after the administration of the last dose, the rats are given an oral dose of $^{51}Cr$-EDTA (10 μCi/rat). The animals are placed individually in metabolism cages with food and water ad lib. Urine is collected for a 24 hr period and $^{51}Cr$ urinary excretion is calculated as a percent of total ingested dose.

Protein-Losing Gastrophathy in Squirrel Monkeys

Rationale

Protein-losing gastropathy (manifested as appearance of circulating cells and plasma proteins in the GI tract) is a significant and dose-limiting adverse response to NSAIDs. This can be quantitatively assessed by intravenous administration or $^{51}CrCl_3$ solution. This isotopic ion can avidly bind to cell and serum globins and cell endoplasmic reticulum. Measurement of radioactivity appearing in feces collected for 24 hr after administration of the isotope thus provides a sensitive and quantitative index of protein-losing gastropathy.

Methods

Groups of male squirrel monkeys (0.8 to 1.4 kg) are treated by gavage with 1% methocel or a test compounds at multiple doses for a few days. Intravenous $^{51}Cr$ (5 μCi/kg in 1 ml/kg PBS) is administered 1 hr after the last drug/vehicle dose, and feces collected for 24 hr in a metabolism cage and assessed for excreted $^{51}Cr$ by gamma-counting. $^{51}Cr$ fecal excretion is calculated as a percent of total injected dose.

Rat Aortic Smooth Muscle Rings in Male Spargue-Dawley Rats

Preparation of Rat Aortic Smooth Muscle Rings Male Sprague-Dawley Rats (Charles River Laboratories (Wilmington, Mass.) are euthanized by intraperiton injection of a high dose of sodium pentobarbitone (80-100 mg/kg). The thoracic aorta is rapidly excised and immediately placed in a Petri dish containing warm (37° C.) oxygenated (95% O, and 5% $CO_2$) Kreb's buffer (composition per millimolar: NaCl (119); KCI (4.69); $CaCl_2.H_2O$ (2.52); $MgSO_4.7H_2O$ (0.57); $NaHCO_2$, (25); $NaH_2PO_.,.H_2O$ (1.01) and glucose (11.1). Under a stereoscopic dissecting microscope, the aorta is cleaned, freed from adhering fat and connective tissues. The tissue is cut into ring segments, each approximately 2-3 mm in length.

For experiments to measure relaxation of the tissue under various conditions, a stainless steel tissue holder and an U-shaped stainless steel wire are inserted into the lumen of the aortic ring. The tissue holder anchored the ring at the bottom of the organ bath whereas the end of the U-shaped steel wire is tied with fine silk thread so that it connected to the FT-202 transducer. The tissue holder and the steel wire along with the aortic ring are then suspended in a 5-ml, double-jacketed temperature-controlled glass organ bath (Radnoti Glass Technology, Inc., Monrovia, Calif.) filled with fresh Kreb's buffer. A mixture of 95% $O_2$ and 5% $CO_2$ is bubbled through a porous sintered disc at the bottom of the bath. The rings are given an initial resting tension of 1.5 g and the preparation is allowed to equilibrate at the initial tension for about 90 minutes. During this equilibration period, the bath fluid is changed every 15-minutes and replaced with fresh prewarmed (37° C.) Kreb's buffer. The isometric tension of the aortic muscle at rest and its response to different stimuli are recorded on a Power Macintosh 6100 computer via a MacLab 8/S computer interface (CB Sciences, Inc, Milford, Mass.) after an initial amplification through a low-noise ETH-400 bioamplifier (CB Sciences, Inc, Milford, Mass.). Contractile responsiveness of the tissue strips is established with 10 TM phenylephrine, and the strips are incubated with the drug for 20 minutes to establish a steady level of contraction.

To test the relaxation effects, test compounds can be added to the phenylephrine precontracted strips in the tissue bath at cumulative concentrations of 0.1 μM to 0.1 mM. Concentration of test compounds may be increased only after relaxation at the previous concentration had reached a plateau level.

Gastric Erosion Model in Rats

The gastric protective effects of the combination of the present invention co-administered with aspirin may be evaluated in the following assay.

Male Wistar rats (200-250 g) were fasted for 16-18 h prior to use for experiment. Aspirin, rofecoxib in combination with aspirin (dosed separately), or test compound in combination with aspirin (dosed separately) were given on the morning of the experiment at a dosing volume of 1 ml/kg in 0.5% methocel. Three hr later, the animals were euthanized by $CO_2$ inhalation and the stomach removed, rinsed in saline and prepared for imaging processing. Microscopic pictures of the stomach were taken using a digital camera and gastric erosions were measured using an imaging software by an observer unaware of the treatment groups. The length of gastric erosions was measured in mm and the total length of all erosions from each stomach was obtained and used as gastric damage score.

This model is also described in S. Fiorucci, et al., Gastroenterology, vol. 123, pp. 1598-1606, 2002 and M. Souza, et al., Am. J. Physiol. Gastrointest. Liver Physiol., vol. 285, pp. G54-G61, 2003.

REPRESENTATIVE EXAMPLES

The invention will now be illustrated by the following non-limiting examples in which, unless stated otherwise:

all operations were carried out at room or ambient temperature, that is, at a temperature in the range 18-25° C.; evaporation of solvent was carried out using a rotary evaporator under reduced pressure (600-4000 pascals: 4.5-30 mm. Hg) with a bath temperature of up to 60° C.; the course of reactions was followed by thin layer chromatography (TLC) and reaction times are given for illustration only; melting points are uncorrected and 'd' indicates decomposition; the melting points given are those obtained for the materials prepared as described; polymorphism may result in isolation of materials with different melting points in some preparations; the structure and purity of all final products were assured by at least one of the following techniques: TLC, mass spectrometry, nuclear magnetic resonance (NMR) spectrometry or microanalytical data; yields are given for illustration only; when given, NMR data is in the form of delta ($\delta$) values for major diagnostic protons, given in parts per million (ppm) relative to tetramethylsilane (TMS) as internal standard, determined at 300 MHz, 400 or 500 MHz using the indicated solvent; conventional abbreviations used for signal shape are: s. singlet; d. doublet; t. triplet; m. multiplet; br. broad; etc.: in addition "Ar" signifies an aromatic signal; chemical symbols have their usual meanings; the following abbreviations have also been used v (volume), w (weight), b.p. (boiling point), m.p. (melting point), L (liter(s)), mL (milliliters), g (gram(s)), mg (milligrams(s)), mol (moles), mmol (millimoles), eq (equivalent(s)).

The following abbreviations have the indicated meanings:

Ac=acetyl
DIBAL=diisobutylaluminum hydride
DMAP=4-(dimethylamino)pyridine
DMF=N,N-dimethylformamide
EDCl=1-(3-dimethylaminopropyl)-3-ethylcarbodiimide hydrochloride
HF.pyr=hydrogen fluoride pyridine (70/30)
TBS=tert-butyl(dimethyl)silyl
TBSCl=tert-butyl(dimethyl)silyl chloride
THF=tetrahydrofuran Alkyl Group Abbreviations Me=methyl
Et=ethyl
t-Bu=tertiary butyl The Dess-Martin reagent, having the following structure, is known in the art.

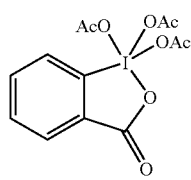

See Dess, D. B.; Martin, J. C., *J. Org. Soc.*, 1983, 48, 4155.

Example 1

(2Z)-4-[({[4,5-bis(nitrooxy)pentyl]oxy}carbonyl)oxy]-3-[4-(methylsulfonyl)phenyl]-2-phenylbut-2-enoic acid

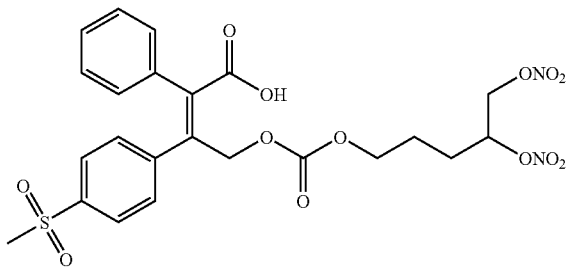

Step 1: 4,5-bis(nitrooxy)pentyl (2Z)-4-hydroxy-2-[4-(methylsulfonyl)phenyl]-3-phenylbut-2-en-1-yl carbonate

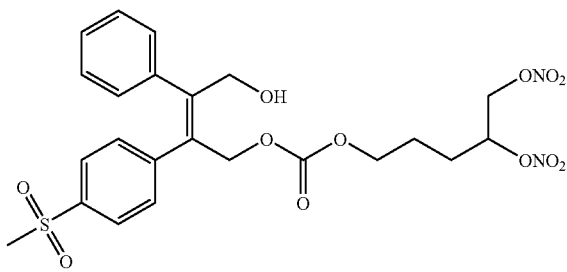

To a solution of 18 ml of phosgene (1.93 M /toluene) at −78° C. under $N_2$, was added 3 g of 3,4-bis(nitrooxy)butyl alcohol. The resulted mixture was stirred at 25° C. for 24 h. Distillation of excess phosgene was done under low vacuum at 50° C. to afford 4.2 g of the desired compound as an orange oil. The crude compound was used directly in the next reaction. To a solution of 3.5 g of (2Z)-4-{[tert-butyl(dimethyl)silyl]oxy}-2-[4-(methylsulfonyl)phenyl]-3-phenylbut-2-en-1-ol, 1.0 g of DMAP and 1.8 mL of Hünig's base in 40 mL of $CH_2Cl_2$ at −78° C. was added 3.3 g of 4,5-bis(nitrooxy)pentyl chloridocarbonate. The reaction mixture was stirred for 2 h at 25° C. and then filtered through a pad of silica gel, washed with EtOAc and evaporated. Purification by flash chromatography afforded 5.4 g of the titled compound as a yellowish oil. The compound was used directly in the next step. To a solution of 5.4 g of 4,5-bis(nitrooxy)pentyl (2Z)-4-{[tert-butyl(dimethyl)silyl]oxy}-2-[4-(methylsulfonyl)phenyl]-3-phenylbut-2-en-1-yl carbonate in 50 mL of acetonitrile was added 2.5 mL of HF.pyr and the mixture was stirred at 25° C. for 1.5 h. The reaction mixture was diluted with 200 mL of toluene, loaded on silica gel and washed with EtOAc. Purification by flash chromatography afforded 4.6 g of the titled compound as a colorless oil. $^1$H NMR (acetone-d6, 500 MHz): $\delta$ 7.69 (d, 2H), 7.34 (d, 2H), 7.14-7.08 (m, 5H), 5.30 (s, 2H), 5.01 (dd, 1H), 4.73 (dd, 1H), 4.64 (d, 2H), 4.17-4.11 (m, 3H), 4.04 (q, 4H), 3.03 (s, 3H), 1.91-1.81 (m, 4H).

Step 2: (2Z)-4-[({[4,5-bis(nitrooxy)pentyl]oxy}carbonyl)oxy]-3-[4-(methylsulfonyl)phenyl]-2-phenylbut-2-enoic acid

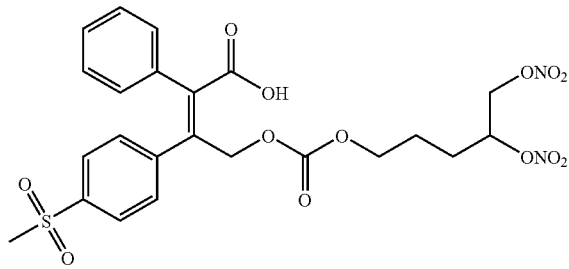

To a solution of 4.5 g of 4,5-bis(nitrooxy)pentyl (2Z)-4-hydroxy-2-[4-(methylsulfonyl)phenyl]-3-phenylbut-2-en-1-yl carbonate in 50 mL of dichloromethane, 4.13 g of Dess-Martin reagent was added and the resulted mixture was stirred at 25° C. for 45 min. Then 250 uL of water was added and the mixture was stirred at RT for 15 min. Then the mixture was filtered through a pad of silica gel and evaporated. The crude was dissolved in a mixture of THF and t-BuOH (25 mL/25 mL). To this solution was added 6.8 mL of 2-methyl-2-butene followed by the addition of 20 mL of phosphoric acid (1.2M soln) and 20 mL of $NaClO_2$ (1M soln). The resulted mixture was stirred at RT for 30 min. The organic phase was separated and the aqueous phase was extracted with EtOAc. The organic phases were combined, dried over $Na_2SO_4$, filtered, and then evaporated. The crude was purified by flash chromatography to afford 2.6 g of the titled compound as white solid. $^1$H NMR (acetone-d6, 500 MHz): δ 7.77 (d, 2H), 7.44 (d, 2H), 7.17 (s, 3H), 7.12 (t, 2H), 5.51 (s, 1H), 5.35 (s, 2H), 5.00 (dd, 1H), 4.72 (dd, 1H), 4.13-4.10 (m, 2H), 3.06 (s, 3H), 1.87-1.80 (m, 4H).

Example 2

Methyl (2Z)-4-[({[4,5-bis(nitrooxy)pentyl]oxy}carbonyl)oxy]-3-[4-(methylsulfonyl)phenyl]-2-phenylbut-2-enoate

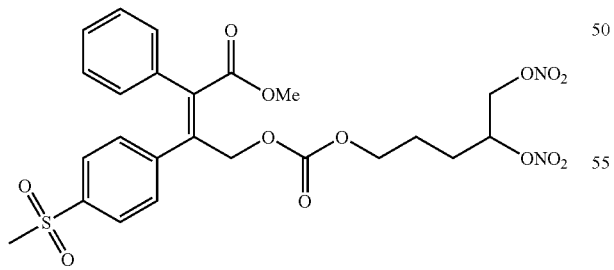

Diazomethane was added to the EXAMPLE 1 to afford 840 mg of the corresponding methyl ester as a colorless oil. $^1$H NMR (acetone-d6, 500 MHz): δ 7.78 (d, 2H), 7.45 (d, 2H), 7.17 (t, 3H), 7.07 (dd, 2H), 5.52-5.49 (m, 1H), 5.26 (s, 2H), 5.00 (dd, 1H), 4.73 (dd, 1H), 4.16-4.11 (m, 2H), 3.79 (s, 3H), 3.06 (s, 3H), 1.92-1.78 (m, 4H).

Example 3

Ethyl (2Z)-4-[({[4,5-bis(nitrooxy)pentyl]oxy}carbonyl)oxy]-3-[4-(methylsulfonyl)phenyl]-2-phenylbut-2-enoate

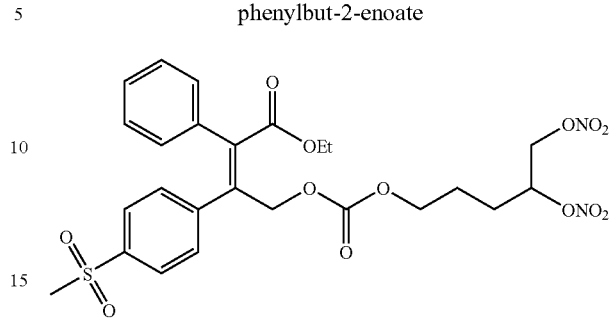

To a solution of 2.6 g (2Z)-4-[({[4,5-bis(nitrooxy)pentyl]oxy}carbonyl)oxy]-3-[4-(methylsulfonyl)phenyl]-2-phenylbut-2-enoic acid in 20 mL of DMF at RT was added 3 mL of ethyl iodide and 485 mg of potassium carbonate under nitrogen. The reaction was stirred for 30 min, and then quenched by addition of $NH_4Cl$ sat., extracted with EtOAc, washed with water (3×), brine and dried over sodium sulfate. Purification by flash chromatography afforded 1.42 g of the titled compound as a colorless oil. $^1$H NMR (acetone-d6, 500 MHz): δ 7.78 (d, 2H), 7.45 (d, 2H), 7.17 (t, 3H), 7.09 (d, 2H), 5.52 (d, 1H), 5.26 (s, 2H), 5.00 (dd, 1H), 4.73 (dd, 1H), 4.28 (q, 2H), 4.16-4.12 (m, 2H), 3.06 (s, 3H), 1.88-1.79 (m, 4H), 1.27 (t, 3H).

Example 4

(2Z)-4-({[2,3-bis(nitrooxy)propoxy]carbonyl}oxy)-3-[4-(methylsulfonyl)phenyl]-2-phenylbut-2-enoic acid

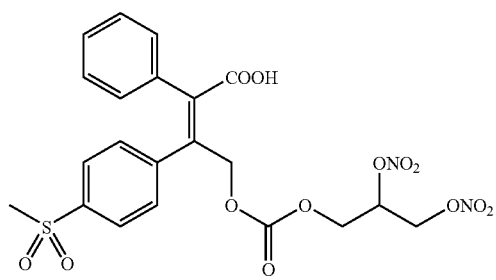

Step 1: (2,2-dimethyl-1,3-dioxolan-4-yl)methyl acetate

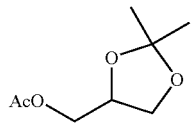

To a solution of 28.1 g (212 mmol) of 2,2-dimethyl-1,3-dioxolane-4-methanol and 44 g (361 mmol) of DMAP in 1 L of dichloromethane was added 36 mL (382 mmol) of acetic anhydride dropwise. The resulting mixture was stirred at rt for 0.5 h. The reaction mixture was then quenched with $NH_4Cl$ (aq), the organic layer separated and washed with saturated $NaHCO_3$. The organic layer was then dried ($Na_2SO_4$), filtered and concentrated in vacuo to give an oil which was used without further purification. $^1$H NMR (500 MHz, acetone-d6): δ 4.30-4.25 (m, 1H), 4.09-4.01 (m, 1H), 3.72 (dd, 1H), 2.01 (s, 3H), 1.33 (s, 3H), 1.27 (s, 3H).

Step 2: 2,3-bis(nitrooxy)propyl acetate

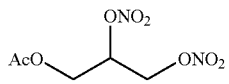

To 15 mL of conc. HNO$_3$ (90%) at −78° C. was added 30 mL of conc. H$_2$SO$_4$ dropwise. The resulting slurry was then warmed briefly to 0° C. where it became a clear colourless solution. The mixture was then cooled back to −78° C. and to this was added dropwise a solution of (2,2-dimethyl-1,3-dioxolanyl)methyl acetate (10 g) in 200 mL dichloromethane. The reaction was then warmed to 0° C. for 0.5 h and then poured onto crushed ice. The organic layer was separated and washed with water (2×) followed by dilute solution of NaHCO$_3$. The organic layer was then dried (Na$_2$SO$_4$), filtered and concentrated in vacuo to give an oil which was used immediately without further purification. $^1$H NMR (500 MHz, acetone-d6): δ 5.78-5.71 (m, 1H), 5.07 (dd, 1H), 4.89 (dd, 1H), 4.58 (dd, 1H), 4.38 (dd; 1H).

Step 3: 3-hydroxypropane-1,2-diyl dinitrate

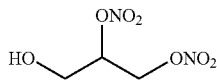

To a solution of 2.5 g of 2,3-bis(nitrooxy)propyl acetate in 25 mL of ethanol at 0. ° C. was added 469 mg of crushed NaOH powder. The reaction was stirred at 0° C. for 15 min upon which a cloudy suspension had formed. The resulting mixture was then poured onto ice cold 5% HCl and then extracted 3× with ether. The organics were combined and evaporated to remove most of the ethanol. The oil was then redissolved in ether, dried (Na$_2$SO$_4$), filtered and concentrated in vacuo to give a pale yellow oil which was used immediately without further purification. $^1$H NMR (500 MHz, acetone-d6): δ 5.59-5.52 (m, 1H), 5.05 (dd, 1H), 4.86 (dd, 1H), 4.60-4.50 (bs, OH), 3.95 (dd, 2H).

Step 4: 2,3-bis(nitrooxy)propyl (2Z)-4-{[tert-butyl (dimethyl)silyl]oxy}-2-[4-(methylsulfonyl)phenyl]-3-phenylbut-2-en-1-yl carbonate

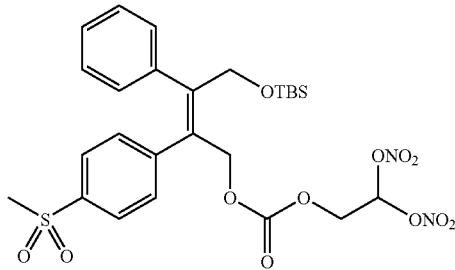

To a −78° C. solution of 2.5 g (13.7 mmol) of 3-hydroxypropane-1,2-diyl dinitrate in 20 mL dichloromethane was added 1.36 g (4.57 mmol) of triphosgene followed by 1.22 mL (15.10 mmol) of pyridine. The resulting mixture was stirred for 5 min at −78° C. then warmed to rt for 15 min upon which the solution turned from cloudy to clear. The above solution was then transferred slowly to a −78° C. solution of 5.64 g (13.04 mmol) (2Z)-4-{[tert-butyl(dimethyl)silyl]oxy}-2-[4-(methylsulfonyl)phenyl]-3-phenylbut-2-en-1-ol and 1.11 mL (13.73 mmol) pyridine in 20 mL of dichloromethane. After complete addition, the reaction mixture was warmed to 0° C. and stirred for an additional 25 min. The reaction was then quenched with NH$_4$Cl (aq) and the organic layer separated, dried (Na$_2$SO$_4$), filtered and concentrated in vacuo to give a yellow oil. Purification by flash chromatography over silica gel (10-80% EtOAc/hexane) afforded 3.73 g of the title compound as an oil. $^1$H NMR (500 MHz, acetone-d6): δ 7.72 (d, 2H), 7.38 (d, 2H), 7.18-7.08 (m, 5H), 5.79-5.75 (m, 1H), 5.35 (s, 2H), 5.05 (dd, 1H), 4.87 (dd, 1H), 4.80 (s, 2H), 4.66 (dd, 1H), 4.49 (dd, 1H), 3.05 (s, 3H), 0.84 (s, 9H), 0.01 (s, 6H).

Step 5: 2,3-bis(nitrooxy)propyl (2Z)-4-hydroxy-2-[4-(methylsulfonyl)phenyl]-3-phenylbut-2-en-1-yl carbonate

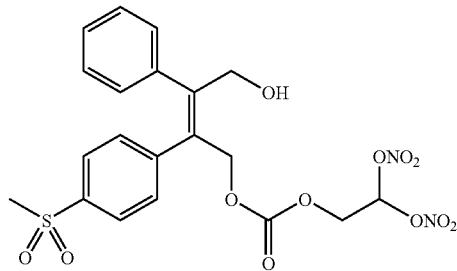

To a 0° C. solution of 3.73 g of 2,3-bis(nitrooxy)propyl (2Z)-4-{[tert-butyl(dimethyl)silyl]oxy}-2-[4-(methylsulfonyl)phenyl]-3-phenylbut-2-en-1-yl carbonate in 150 mL of MeCN was added 5 mL of 70% PyHF. The resultant mixture was allowed to warm to rt and stirred for an additional 4 h. The reaction mixture was diluted with 600 mL of toluene and filtered through a plug of silica gel, eluting with EtOAc. The filtrate was concentrated and the resulting residue was further purified by flash chromatography over silica gel (10-50% EtOAc/hexane) to afford 3.1 g of the title compound along with a 20% impurity. $^1$H NMR of major compound (500 MHz, acetone-d6): δ 7.72 (d, 2H), 7.37 (d, 2H), 7.17-7.11 (m, 5H), 5.79-5.73 (m, 1H), 5.38 (s, 2H), 5.05 (dd, 1H), 4.87 (dd, 1H), 4.68-4.65 (m, 3H), 4.49 (dd, 1H), 4.15 (t, 1H), 3.05 (s, 3H).

Step 6: (2Z)-4-({[(2,3-bis(nitrooxy)propoxy] carbonyl}oxy)-3-[4-(methylsulfonyl)phenyl]-2-phenylbut-2-enoic acid

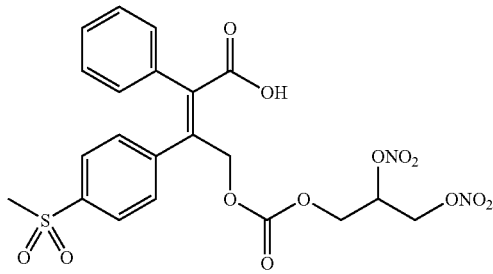

To a solution of 3.1 g of 2,3-bis(nitrooxy)propyl (2Z)-4-hydroxy-2-[4-(methylsulfonyl)phenyl]-3-phenylbut-2-en-1-yl carbonate in 30 mL of dichloromethane was added 3.1 g of Dess-Martin reagent and the resultant mixture was stirred at rt for 2 h. Then 3 mL of water was added and the resultant mixture was stirred at rt for 0.5 h. The cloudy mixture was then filtered and filtrate extracted 3× with EtOAc. The organic layers were combined, dried (Na$_2$SO$_4$), filtered and concentrated in vacuo to give a pale yellow residue. The crude material was then dissolved in a solvent mixture of 5 mL of THF with 5 mL of t-BuOH and to this was added 2 mL of 2-methyl-2-butene followed by the addition of 2 mL of 1 M of phosphoric acid and 1.16 g of NaClO$_2$. The reaction mixture was stirred at rt for 3.5 h. The organic phase was separated and the aqueous phase was extracted with EtOAc. The combined organic layer was dried (Na$_2$SO$_4$), filtered, and then concentrated in vacuo. The crude was purified by recrystallization from warm ether to afford 1.23 g of the title compound as a white solid. $^1$H NMR (500 MHz, acetone-d6): δ 7.79 (d, 2H), 7.47 (d, 2H), 7.22-7.14 (m, 5H), 5.75-5.72 (m, 1H), 5.43 (s, 2H), 5.03 (dd, 1H), 4.83 (dd, 1H), 4.63 (dd, 1H), 4.47 (dd, 1H), 3.08 (s, 3H).

Example 5 ethyl (2Z)-4-({[2,3-bis(nitrooxy)propoxy] carbonyl}oxy)-3-[4-(methylsulfonyl)phenyl]-2-phenylbut-2-enoate

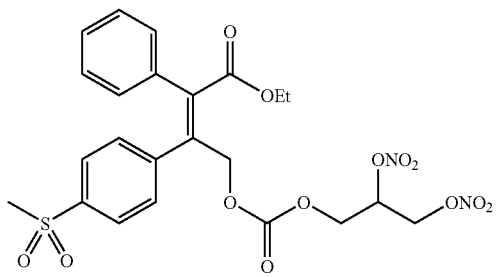

To a 0° C. solution of 454 mg of (2Z)-4-({[2,3-bis(nitrooxy)propoxy]carbonyl}oxy)-3-[4-(methylsulfonyl)phenyl]-2-phenylbut-2-enoic acid in 20 mL of THF was added excess diazoethane in diethylether until crude NMR revealed complete conversion to ethyl ester. Evaporation of the solvent followed by flash chromatography of the crude residue over silica gel (30-90% EtOAc/hexane) afforded 420 mg of the title compound as a clear colourless oil. $^1$H NMR (500 MHz, acetone-d6): δ 7.80 (d, 2H), 7.49 (d, 2H), 7.23-7.18 (m, 3H), 7.14-7.08 (m, 2H), 5.79-5.73 (m, 1H), 5.35 (s, 2H), 5.05 (dd, 1H), 4.85 (dd, 1H), 4.64 (dd, 1H), 4.47 (dd, 1H), 4.31 (q, 2H), 3.08 (s, 3H), 1.29 (t, 3H).

Example 6 benzyl (2Z)-4-({[2,3-bis(nitrooxy)propoxy] carbonyl}oxy)-3-[4-(methylsulfonyl)phenyl]-2-phenylbut-2-enoate

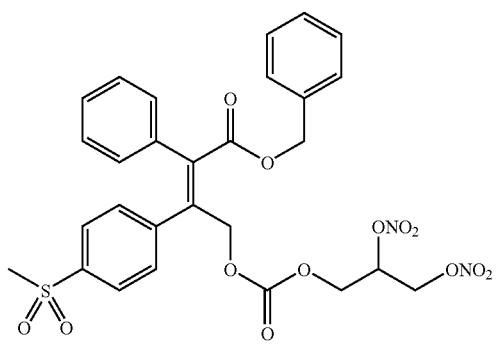

To 300 mg of (2Z)-4-({[2,3-bis(nitrooxy)propoxy] carbonyl}oxy)-3-[4-(methylsulfonyl)phenyl]-2-phenylbut-2-enoic acid in 5 mL of DMF was added 69 μL benzyl bromide followed by 81 mg of potassium carbonate (325 mesh). The resulting mixture was stirred at rt for 30 min. The reaction was then quenched with saturated solution of NH$_4$Cl and extracted with Et$_2$O/hexanes (½, 2 times). The combined organic extracts were dried (Na$_2$SO$_4$), filtered and concentrated in vacuo to give a pale yellow residue. Flash chromatography of the crude material over silica gel (10-70% EtOAc/hexane) afforded 250 mg of the title compound as a white solid. $^1$H NMR (500 μL, acetone-d6): δ 7.80 (d, 2H), 7.48 (d, 2H), 7.42-7.35 (m, 5H), 7.21-7.18 (m, 3H), 7.13-7.10 (m, 2H), 5.77-5.73 (m, 1H), 5.36 (s, 2H), 5.33 (s, 2H), 5.04 (dd, 1H), 4.84 (dd, 1H), 4.64 (dd, 1H), 4.48 (dd, 1H), 3.08 (s, 3H).

What is claimed is:
1. A compound of Formula I

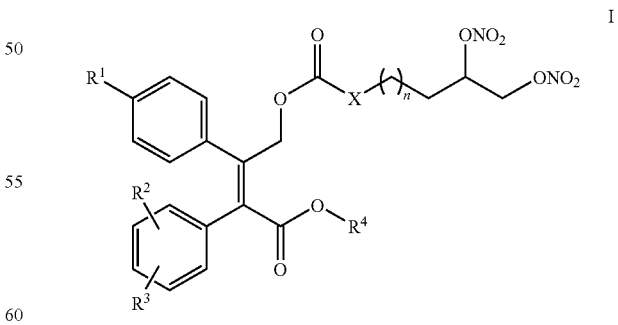

or a pharmaceutically acceptable salt thereof, wherein:
n is an integer from 1 to 6;
X is —O— or —CH$_2$—;
R$^1$ is selected from the group consisting of:
(a) S(O)$_2$CH$_3$ and
(b) S(O)$_2$NH$_2$;

R² and R³ each are independently selected from the group consisting of:
(a) hydrogen,
(b) halo,
(c) $C_{1-6}$alkoxy,
(d) $C_{1-6}$alkylthio,
(e) CN,
(f) $CF_3$,
(g) $C_{1-6}$alkyl, and
(h) $N_3$;

R⁴ is selected from the group consisting of
(a) hydrogen,
(b) —$C_{1-4}$alkyl, optionally substituted with with 1 to 3 substituents independently selected from halo and R⁵, and
(c) R⁵;

each R⁵ is independently selected from the group consisting of: phenyl, naphthyl or a 5- or 6-membered aromatic heterocycle, each optionally substituted with 1 to 3 halo groups.

2. The compound according to claim 1 wherein
R¹ is $S(O)_2CH_3$, and
R² and R³ are both hydrogen.

3. The compound according to claim 1 wherein n is 1, 2 or 3.

4. The compound according to claim 1 wherein R⁴ is selected from the group consisting of: hydrogen, methyl, ethyl and benzyl.

5. The compound according to claim 1 wherein X is —O—.

6. A method of treating an inflammatory disease wherein the disease is selected from the group consisting of osteoarthritis, rheumatoid arthritis and chronic pain comprising administering to a patient in need of such treatment of a non-toxic therapeutically effective amount of a compound according to claim 1.

7. The method according to claim 6 wherein the patient is also at risk of a thrombotic event and the patient is on aspirin therapy to reduce the risk of the event.

8. The method according to claim 7 wherein the compound is administered orally on a once daily basis.

9. The method according to claim 7 wherein the compound is administered orally on a twice daily basis.

10. The method according to claim 7 wherein aspirin is administered at a dose of about 30 mg to about 1 g.

11. The method according to claim 10 wherein aspirin is administered at a dose of about 80 to about 650 mg.

12. The method according to claim 11 wherein aspirin is administered at a dose of about 81 mg or about 325 mg.

13. The method according to claim 7 wherein aspirin is orally administered once daily.

14. A pharmaceutical composition comprising a compound according to claim 1 and aspirin in combination with a pharmaceutically acceptable carrier.

15. A pharmaceutical composition comprising a compound according to claim 1 and a pharmaceutically acceptable carrier.

* * * * *